(12) United States Patent
Klapproth

(10) Patent No.: US 6,921,669 B2
(45) Date of Patent: Jul. 26, 2005

(54) LINKER SYSTEM FOR ACTIVATING SURFACES FOR BIOCONJUGATION

(75) Inventor: Holger Klapproth, Freiburg (DE)

(73) Assignee: Micronas Holding GmbH, Freiburg (DE)

( * ) Notice: Subject to any disclaimer, the term of this patent is extended or adjusted under 35 U.S.C. 154(b) by 0 days.

(21) Appl. No.: 10/030,999

(22) PCT Filed: May 16, 2001

(86) PCT No.: PCT/EP01/05557

§ 371 (c)(1),
(2), (4) Date: Jan. 16, 2002

(87) PCT Pub. No.: WO01/88535

PCT Pub. Date: Nov. 22, 2001

(65) Prior Publication Data

US 2003/0022189 A1 Jan. 30, 2003

(30) Foreign Application Priority Data

May 16, 2000 (EP) ............................................ 00110428

(51) Int. Cl.$^7$ .................... G01N 33/533; G01N 33/534; G01N 33/535; G01N 33/552; G01N 33/553; C07K 17/04; C12K 1/68

(52) U.S. Cl. ........................ 436/527; 436/525; 436/532; 436/545; 436/546; 436/161; 435/6; 435/7.5; 435/7.72; 435/7.92; 435/188; 530/391.1; 530/402

(58) Field of Search ................................ 436/525, 527, 436/532, 545, 546, 161, 14, 535; 435/6, 7.5, 7.92, 7.72, 188; 530/402, 391.1; 549/555

(56) References Cited

FOREIGN PATENT DOCUMENTS

| JP | 08220673 A2 | * | 8/1996 |
|----|----|----|----|
| WO | 95/01987 A1 | * | 1/1995 |
| WO | 99/07744 A1 | * | 2/1999 |
| WO | 99/17120 A1 | * | 4/1999 |
| WO | WO-99-36571 A | | 7/1999 |

OTHER PUBLICATIONS

S. Zalipsky, Bioconjugate Chemistry (1995), vol. 6, pp. 150–165. Functionalized Poly(ethylene glycol) for Preparation of Biologically Relevant Conjugates.*
C. Bertozzi et al, J. Org. Chem. (1991), vol. 56, pp. 4326–4329. The Synthesis of Heterobifunctional Linkers for the Conjugation of Ligands to Molecular Probes.*
Nucleic Acids Research, vol. 27, No. 9, 1999, pp. 1970–1977, XP002145887, M. Beier et al., "Versatile Derivatisati on of Solid Support Media for Covalent . . . ".
Nucleic Acids Research, vol. 24, No. 15, 1996, pp. 3031–3039, XP002149193, L.A. Chrisey et al., "Covalent Attachment of Synthetic DNA to Self–Assembled . . . ".
Analytical Chemistry, 1998, vol. 70, No. 13, pp. 2731–2736, XP002111582, C.P. Sonksen et al., "Combining Maldi Mass Spectrometry and Biomolecular Interaction Analysis Using a Biomolecular Interaction Analysis Instrument".
Angewandte Chemie, 2000, vol. 112, No. 8, Summary of pp. 1970–1977, I. Willner et al., "Integration of Layered Redox Proteins and Conductive Supports . . . ".
NATURE, vol. 256, Aug. 7, 1975, pp. 495–497, G. Kohler et al., "Continuous cultures of fused cells secreting a ntibody of predefined specifici ty".
VIROLOGY, vol. 176, 1990, pp. 604–619, Larry T. Mimms et al., "Discrimination of Hepatitis B Virus (HBV) Subtypes Using Monoclonal Antibodies . . . ".
Bioconjugate Techniques, Academic Press 1886, pp. 137–168, G. T. Hermanson, "The Chemistry of Reactive Groups".
A. Maciejewski et al., "Relaxation of the second excited singlet states of aromatic thiones" Journal of the American Chemical Society, May 15, 1985, vol. 107, No. 10, pp. 2831–2837.

* cited by examiner

Primary Examiner—Mary E. Ceperley
(74) Attorney, Agent, or Firm—Griffin & Szipl, P.C.

(57) ABSTRACT

The present invention relates to a linker system for activating surfaces for bioconjugation, and particularly to a linker system having a novel hydrophilic spacer group. The inventive linker system may be used for the construction of sensor chips or biochips for the detection of sample biomolecules.

9 Claims, No Drawings

LINKER SYSTEM FOR ACTIVATING SURFACES FOR BIOCONJUGATION

The present invention relates to a linker system for activating surfaces for bioconjugation, and particularly to a linker system having a novel hydrophilic spacer group.

Due to the steadily growing importance of micro techniques in a wide variety of scientific applications, the development of systems which allow the interaction of molecules with surfaces remains a critical issue. Such interactions include the possibility of removing specific molecules from a sample, e.g. to facilitate their analysis/detection, but also of presenting molecules on a surface, thus allowing subsequent reactions to take place. These principles for the immobilization of molecules can be applied in sensor or chromatographic systems or for the provision of modified surfaces in general.

In recent years there have been numerous approaches to fabricate sensor chips or biochips which are based on self-assembled monolayers (SAM's) of bifunctional molecules which directly or indirectly couple sample molecules to the sensor surface. Typically, these bifunctional molecules carry for example a silane or thiol/disulfide moiety in order to achieve a bond with the inorganic surface and an additional functional group (e.g. amino groups or epoxide groups) which interact with sample molecules, often contained in biological samples in the form of an oligonucleotide, a protein or a polysaccharide etc.

While the formation of a direct bond between the bifunctional compound and the sample molecule is possible, the sample molecules do not necessarily interact directly with the linkers or couplers, respectively, forming the monolayer. Alternatively, appropriate immobilized biomolecules themselves can act as probes for the detection of sample molecules Such probe molecules can equally be immobilized via a reaction with the free functional groups of the monolayer. In particular, if biomolecules are used as probe molecules, their presence may significantly enhance the specificity of the interaction of the sample molecules with the modified surface.

Although these techniques are well established for this purposes the application of standard detection methods is problematic, especially in cases where the surface area available for the detection of one specific type of sample molecules is restricted, e.g. if a variety of molecules is to be analyzed in a parallel process, since the monolayers are limited in their graft density. Thus, suitable detectors have to meet very high requirements with regard to their sensitivity, and the minimum surface area on a sensor necessary for the detection of one type of sample molecule cannot be easily reduced.

Moreover, the maximum density, i.e. one sample or probe molecule per functional group of the linkers or couplers, respectively, can hardly be attained, since due to sterical hindrance on the two-dimensionally extended monolayer, only a fraction of the functional groups will be able to react with sample or probe molecules. Thus, the overall graft density is low and normally not well defined.

For the preparation of the above-mentioned sensor chips or biochips which are normally employed in aqueous environments appropriately hydrophilic layers functionalized/activated for conjugation with sample or probe molecules are often used. These hydrophilic layers are, in contrast to hydrophobic layers, wettable and thus have a better printability for applying onto a respective surface, for example in the form of a patterned array.

In case of coupling to a silicon oxide or derived substrate, e.g. a glass surface etc., commonly aminosilanes, e.g. tri-methoxysilylpropylamine (APTF), are used in a first step for modification (silanization) of the surface. In a second step of activating said surface the free amino groups of the aminosilanes are functionalized with a heterobifunctional cross-linker capable of covalently binding to the desired sample or probe molecule, e.g. succinimidyl 4-[mateimidophenyl] butyrate (SMPB) in case of thiol-modified DNA oligomers (cf. Chrisey, Lee and O'Ferrell, Nucleic Acids Research, 1996, Vol 24. No. 15, pp. 3031–3039).

The above-mentioned aminosilane based method, however, has the disadvantages that the reaction steps following silanization result in a reduced maximum grafting density, and that the method as such is laborious and difficult to control. Further, the resulting hydrophilic layers are in the biologically suitable pH range positively charged. It is not possible to obtain negatively charged or uncharged layers. A strong positive charge would cause a strong unspecific absorption of negatively charged molecules and a strong repellation of positively charged molecules.

While various attempts have been made to overcome the problems of the aminosilane based method outlined above there is still a need for alternative positive hydrophilic layers, and particularly for negatively charged or uncharged hydrophilic layers. With these different types of layers the surface may easily be adapted to the particular analytical problem.

Accordingly, it is an object of the present invention to provide such alternative positive hydrophilic layers, and in particular to provide negatively charged or uncharged hydrophilic layers.

These and other objects and features of the invention will be apparent from the description and claims which follow.

Accordingly, the invention provides as per claim 1 a linker system for activating surfaces for bioconjugation having the following general formula (I):

$$X\text{—}[(Y_1)_i\text{—}Q\text{—}(Y_2)_j]_k\text{—}Z \qquad (I)$$

wherein X is a reactive group capable of covalently binding to a surface, Z is a reactive group capable of covalently binding to a biomolecule, with the proviso that X is not Z, $Y_1$ and $Y_2$ are independently from each other $CR_1R_2$ with $R_1$ and $R_2$ being independently from each other H, $C_1$–$C_4$ alkyl, $C_1$–$C_4$ alkoxy or $C_1$–$C_4$ acyloxy, i, j, k are independently from each other an integer in the range from 1 to 10, with the proviso that the total number of C atoms in $Y_1$ and $Y_2$, the C atoms of $R_1$ and $R_2$ not included, is in the range of 2 to 100, and Q is a hydrophilic atom or group selected from the group consisting of O, NH, C=O, O—C=O and $CR_3R_4$, wherein $R_3$ and $R_4$ are independently from each other selected from the group consisting of H, OH, $C_1$–$C_4$ alkoxy and $C_1$–$C_4$ acyloxy, with the proviso that $R_3$ and $R_4$ are not H at the same time and that for Q=NH Z is not $NH_2$, and wherein in the case of k>1 the Q's for each $[(Y_1)_i$-Q-$(Y_2)_j]_k$ are independently selected from each other.

The inventive linker system allows the preparation of positively or negatively charged or uncharged layers on the substrate which have a good wettability. Further, after coupling to the surface, for example by silanization, no further steps are required, for example coupling with a bifunctional linker, to built up the final linker system resulting in an improved graft density. For example, if Z is an epoxy group, which reactive group may be introduced directly, the inventive linker system may directly bind to biomolecules such as DNA. In addition, the inventive linker system can easily be printed on a surface by using conventional printing techniques, for example as detailed below.

Further advantageous or preferred embodiments are subject-matter of the subclaims.

In the following more detailed description of the invention the disclosure content of the documents cited throughout the specification is incorporated herewith by reference.

In the above linker system said reactive group X is not particularly limited and may be selected according to the practical situation, i.e. the surface the binding to which is intended for. For example, thiol and disulfide groups may bind to gold surfaces, alkoxy- or halogensilanes may bind to glass and ceramic surfaces, and groups capable of forming free radicals, for example on exposure to light such as UV light, may bind to plastic surfaces, i.e. comprising organic polymers.

For example said reactive group X is selected from the group consisting of a disulfide group (—SS—), a thiol or mercapto group (—SH), a silane group $SiW_3$ with W being a hydrolysable atom or group, and a group capable of forming free radicals, for example on exposure to light, such as an anthrathione group or a derivative thereof, an anthraquinone group or a derivative thereof, a benzophenone group or a derivative thereof.

Preferably said hydrolysable atom or group W is selected from the group consisting of halides such as Cl, Br, I and F, $C_1$–$C_4$ alkoxy groups such as methoxy, ethoxy, propoxy, iso-propoxy, n-butoxy, iso-butoxy or tert-butoxy groups, $C_1$–$C_4$ acyloxy such as formyl, acetyl, propionyl, iso-propionyl, n-butyryl, iso-butyryl or tert-butyryl groups and amino groups.

Further suitable reactive groups X are for example described in the textbook "Bioconjugate Techniques" by G. T. Hermanson, Academic Press, 1996. As examples for original papers in this regard there might be mentioned Chrisey, Lee and O'Ferrell, Nucleic Acids Research, 1996, Vol. 24, No. 15, pp. 3031–3039; or Beier and Hoheisel, Nucleic Acids Research, 1999, Vol. 27, No. 9, pp. 1970–1977, disclosing in particular ETA, PEDA as defined therein, which are also suitable in the invention.

As already defined above $Y_1$ and $Y_2$ may be independently from each other $CR_1R_2$ with $R_1$ and $R_2$ being independently from each other H, $C_1$–$C_4$ alkyl, for example methyl, ethyl, propyl, iso-propyl, butyl, iso-butyl or tert-butyl; or $C_1$–$C_4$ alkoxy, for example, methoxy, ethoxy, propoxy, iso-propoxy, n-butoxy, iso-butoxy or tert-butoxy; or $C_1$–$C_4$ acyloxy such as formyl, acetyl, propionyl, iso-propionyl, n-butyryl, iso-butyryl or tert-butyryl.

The indices i, j, k are independently from each other an integer in the range from 1 to 10, with the proviso that the total number of C atoms in $Y_1$ and $Y_2$, the C atoms of $R_1$ and $R_2$ not included, is in the range of 2 to 100, for example 2 to 80, or 2 to 60, or 2 to 40, or 2 to 20, in particular 2 to 18, or 2 to 16, or 2 to 14, or 2 to 12, or 2 to 10, or 2 to 8.

In this context it should be noted that the sole reason for the above proviso is, that an ideal distance of a DNA to a hydrophobic surface is known to be about 100 carbon atoms. Thus, there is actually no maximum spacer length for any chemical reasons but a maximum appropriate or useful spacer length. On the other hand, it is also known that the longer the spacer the lower the graft density.

Specific examples for $Y_1$ and $Y_2$, which may be the same or different from each other, are depending from the respective values of i and j methylene, ethylene, tri-, tetra-, penta-, hexa-, hepta-, octa-, nona- or decamethylene groups, which in addition may be branched or substituted as defined above for $R_1$ and $R_2$. Is to be understood that $Y_1$ and $Y_2$ do not have such a chain length that solidification results, or are so extensively branched that formation of monolayers on a surface is inhibited or prevented. The same is true in the case of k>1 for each "repeating block" $[(Y_1)_i\text{-}Q\text{-}(Y_2)_j]_k$.

Q is a hydrophilic atom or group which is not particularly limited as long as its function of imparting hydrophilicity to the inventive linker system is not affected. In general, hydrophilicity may result from polarization of a molecule by the electron-attracting action of atoms being more electronegative than carbon atoms. For example, hydrophilic atoms or groups are capable of forming hydrogen bonds or bridges in an aqueous environment resulting in hydration, which leads to an improved accessibility for hydrophilic molecules.

Suitable hydrophilic atoms or groups for use in the inventive linker system are selected from the group consisting of O, NH, C=O (keto group), O—C=O (ester group) and $CR_3R_4$, wherein $R_3$ and $R_4$ are independently from each other selected from the group consisting of H, OH, $C_1$–$C_4$ alkoxy and $C_1$–$C_4$ acyloxy with the proviso that $R_3$ and $R_4$ are not H at the same time and that for Q=NH Z (as defined below) is not $NH_2$.

Specific examples for $C_1$–$C_4$ alkoxy are methoxy, ethoxy, propoxy, iso-propoxy, n-butoxy, iso-butoxy or t-butoxy. Specific examples for $C_1$–$C_4$ acyloxy are formyl, acetyl, propionyl, iso-propionyl, n-butyryl, iso-butyryl or tert-butyryl. Further, it is to be understood that $CR_3R_4$ as Q is not so extensively branched that formation of monolayers on a surface is inhibited or prevented.

For Q also S (sulfur) or S—S (disulfide) might be considered, but are, however, not preferred since the resulting compounds are in general malodorous. In addition, disulfide bridges may be easily reduced resulting in a breakage of the linker system.

Further, in the case of k>1 the Q's for each "repeating block" $[(Y_1)_i\text{-}Q\text{-}(Y_2)_j]_k$ may be independently selected from each other.

In the above linker system said reactive group Z is not particularly limited and may be selected according to the practical situation, i.e. the sample or probe molecule the binding to which is intended for. Since most of the sample or probe molecules, especially in biological or medical applications, comprise sterically unhindered nucleophilic moieties, preferred reactions with said molecules comprise nucleophilic substitution or nucleophilic addition reactions or Diels-Alder reactions leading to a covalent bond between the reactive group Z of the inventive linker system and the sample or probe molecules. Further, also radical substitution is possible.

It might be appreciated that the above reactive group Z either represents the one necessary for the interaction with the sample or probe molecules, or can be transformed to such a suitable reactive group in a further step. Further, reactive group Z may be hydrophobic per se subject to that the character of the linker system as a whole is still hydrophilic.

For example said reactive group Z is selected from the group consisting of a reactive double bond such as in an acrylic moiety, a diene group such as in butadiene, a dienophilic group such as in maleic anhydride or maleinimide, an epoxy group such as in glycidyl derivatives, an aldehyde group, a hydroxyl group, a carboxylic acid group, an active or reactive ester group such as in N-hydroxysuccinimidyl(NHS)-esters or imidoesters or azlactone, an amino group (—$NH_2$), a disulfide group (—S—S—), a thiol or mercapto group (—SH), an aziridine group, an isocyanate group (—N=C=O), an isothiocyanate group (—N=C=S), an azide group and a reactive leaving group such as NHS.

Further suitable reactive groups Z are for example described in the textbook "Bioconjugate Techniques" by G. T. Hermanson, Academic Press, 1996. As examples for original papers in this regard there might be mentioned Chrisey, Lee and O'Ferrell, Nucleic Acids Research, 1996, Vol. 24, No. 15, pp. 3031–3039; or Beier and Hoheisel, Nucleic Acids Research, 1999, Vol. 27, No. 9, pp. 1970–1977, disclosing in particular PDITC, DSC, DSO, DMS, SMPB, MBS, SMCC, GMBS, MPS and SIAB as defined therein, which are also suitable in the invention.

A specific example for an inventive linker system has the following formula:

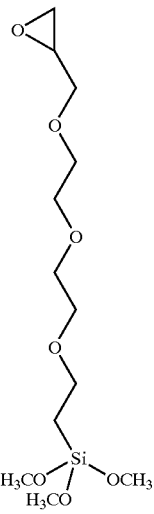

In a further aspect the invention provides a surface carrying an inventive linker system.

The shape, size or chemical composition of the surface is not particularly limited and may be selected according to the practical situation. For example the surface may be part of a container or may form beads, granules, sheets, plates or films, for example on a suitable substrate. Regarding its chemical composition the surface may for example be selected from the group consisting of a $SiO_2$ surface (including evaporated or sputtered SiOx layers), for example of a silicon wafer, of glass, quartz, fused silica etc. (which $SiO_2$ surfaces may also contain other oxides such as $B_2O_3$, $Al_2O_3$ etc.), gold and a polymer or a plastic such as cycloolefin copolymers (COCs), poly(methyl methacrylate) (PMMA, plexiglass), polystyrene, polyethylene and polypropylene. A suitable COC is for example available from Ticona under the trade name "Topaz".

In a preferred embodiment the inventive linker system forms a patterned array on a surface, e.g. a solid surface.

The creation of patterned arrays of the inventive linker system on a surface is possible by various means, for example by applying standard photolithographic processes, by using micro contact printing or related methods, ink jet techniques or other micro plotting methods. By using any of these techniques, surface structures with dimensions in the micrometer range can be created. For sensor chips or biochips using appropriate labels as detailed below the high parallel mode of signal generation and a significant improvement in the integration of analytical data is the most promising feature of such techniques, which accordingly allow the optimization of automatic analytical procedures.

In another preferred embodiment the surface attached inventive linker system is covalently bonded to a biomolecule, e.g. for use as a probe for a sensor chip or biochip.

The above-mentioned biomolecule is not particularly limited and may be selected according to the practical situation. For example the biomolecule is a partner of a specifically interacting system of complementary binding partners for improving selectivity of binding in a complex mixture of components such as a biological fluid.

The term "interacting", as used in this specification, includes the formation of covalent bonds, as well as attractive ionic and van-der-Waal's forces and hydrogen bonds.

For example said specifically interacting system of complementary binding partners is based on nucleic acid/complementary nucleic acid, peptide nucleic acid(PNA)/nucleic acid, enzyme/substrate, receptor/effector, lectin/sugar, antibody/antigen, avidin/biotin or streptavidin/biotin interaction.

The above nucleic acids may be a DNA or RNA, for example an oligonucleotide or an aptamer.

The above antibody may be, but is not restricted to, a polyclonal, monoclonal, chimeric or single-chain antibody or a functional fragment or derivative of such antibodies In another aspect the invention relates to a process for the detection of a biomolecule which is a partner of a specifically interacting system of complementary binding partners comprising the steps of a) contacting a surface comprising an inventive linker system having covalently attached thereto one partner of a specifically interacting system of complementary binding partners, e.g. a nucleic acid or an antibody, with a sample suspected to contain the complementary binding partner, e.g. a complementary nucleic acid or an antigen, b) removing non-specifically bound sample components in a washing step, and c) detecting the specifically bound sample components.

The detection method is not particularly limited and may be selected according to the practical situation. For example, a colored, fluorescent, bioluminescent, chemoluminescent, phospho-rescent or radioactive label, an enzyme (e.g. in the form of an ELISA assay), an antibody or a functional fragment or derivative thereof, a protein A/gold based system, a biotin/avidin or biotin/streptavidin based system or an enzyme electrode based system may be used.

The above detection systems are well-known in the art, see for example F. Lottspeich und H. Zorbas (Eds) in "Bioanalytik", Spektrum Akademischer Verlag Heidelberg 1998. Thus, a detailed description may be dispensed with. Suitable electrochemically or enzyme electrode based systems are described in Angewandte Chemie, 2000, Vol. 112, No. 7, pp. 1230–1269.

Depending on the labeling method applied, the detection can be effected by methods known in the art, e.g. via laser scanning or use of CCD cameras.

Further, so-called indirect methods of detection may be applied. An example of such an indirect detection is the use of a secondary labeled antibody (anti-antibody) directed to a first unlabeled antibody which binds to the biomolecule (sample molecule) of interest.

In yet another aspect the invention relates to a process for the isolation of a biomolecule which is a partner of a specifically interacting system of complementary binding partners comprising the steps of a) contacting a surface comprising an inventive linker system having covalently attached thereto one partner of a specifically interacting system of complementary binding partners, e.g. a lectin or an antibody, with a sample suspected to contain the complementary binding partner, e.g. a sugar or an antigen, b) removing non-specifically bound sample components in a washing step, and, optionally, c) eluting the specifically bound sample components, for example by using a chaotropic agent.

The invention further comprises the use of a surface as defined above as an affinity matrix, for example as a stationary phase for chromatographic purposes, or for providing a sensor chip or biochip. The sensor chip or biochip may be part of a medical or diagnostic instrument, which for example may be used for the detection of components in physiological fluids, such as blood, serum, sputum etc.

A regeneration of the inventive surfaces after binding of the linked probe to the respective sample biomolecule to be detected or isolated has taken place is possible, but single uses are preferred in order to ensure the quality of results, in particular in case of detection uses (sensor chips or biochips).

With sensor chips or biochips using an inventive surface as defined above different types of samples can be analyzed with an increased precision and/or reduced need of space in serial as well as parallel detection methods.

In general, the coupling reaction between the linker system of the invention and the molecules to be detected or isolated is performed under conditions which are not detrimental to the sample or probe molecules.

For example, in a nucleic acid sensor application, the reaction should be carried out in an aqueous solution, and the temperature should not be raised above 95° C. Preferably the temperature is in the range of 40–60° C.

Also, the coupling reaction with the sample or probe biomolecule should proceed at a reasonable rate so that the detection can preferably be accomplished within less than 24 hours without requiring extreme pH-values in the solution. For the immobilization of single strands of synthetic oligonucleotides as a probe, the pH should range between 7 and 11, preferably 7 to 10.

During the hybridization reaction of the nucleic acid sample molecules with the probe molecules, the bonds between the functional group and the synthetic oligonucleotide single strands as well as the bonds of the linker system to the substrate have to be able to withstand temperatures of more than 65° C., and a pH of 6–9. In cases where DNA is used as a sample molecule, the temperatures may have to be raised up to about 95° C. in order to effect a separation of the DNA strands, which is necessary for hybridization.

Suitable hybridization conditions may be established according to conventional protocols described, for example, in Sambrook, "Molecular Cloning, A Laboratory Manual", Cold Spring Harbor Laboratory, N.Y. (1989); Ausubel, "Current Protocols in Molecular Biology", Green Publishing Associates and Wiley Interscience, N.Y. (1989); or Higgins and Hames (Eds) "Nucleic acid hybridization, a practical approach" IRL Press Oxford, Washington D.C., (1985).

The setting of conditions is well-known to the skilled artisan and to be determined according to protocols described in the art. Thus, the detection of only specifically hybridizing sequences will usually require stringent hybridization and washing conditions such as for example 0.1× SSC, 0.1% SDS at 65° C. Exemplary non-stringent hybridization conditions for the detection of homologous or not exactly complementary sequences may be set at 6× SSC, 1% SDS at 65° C.

As is well known, the length of the probe and the composition of the nucleic acid to be determined constitute further parameters of the hybridization conditions.

The nucleic acids to be analyzed may originate from a DNA library or a genomic library, including synthetic and semisynthetic nucleic acid libraries.

For an example of a protein sensor chip application an antibody as defined above may be attached to the inventive linker system.

The general methodology for producing antibodies is well-known and has been described in, for example, Köhler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982). A further methodology is that taught by L. T. Mimms et al., Virology 176 (1990), 604–619.

As already stated above the term "antibody" relates to monoclonal or polyclonal antibodies. Functional antibody fragments or derivatives provide the same specificity as the original antibody and comprise $F(ab')_2$, Fab, Fv or scFv fragments; see, for example, Harlow and Lane, "Antibodies, A Laboratory Manual", CSH Press 1988, Cold Spring Harbor, N.Y. Derivatives of an antibody can, for example, be produced by peptidomimetics. Such production methods are well known in the art and can be applied by the skilled artisan without further ado.

In the following the invention is disclosed in more detail with reference to examples. However, the described specific forms or preferred embodiments are to be considered in all respects as illustrative and not restrictive, the scope of the invention being indicated by the appended claims rather than by the following description, and all changes which come within the meaning and range of equivalency of the claims are therefore intended to be embraced therein.

EXAMPLES

Synthesis of {1-[2-{glycydyl)-ethoxy]-ethoxy}-trimethoxysilane (GEETS)

Synthesis of silanes belongs to the state of the art. The sample silane is synthesised by addition of 1,7-bromdiethylenglycol to glycidol, for example by addition of 1 mol glycydol to a 1.5 molar solution of 1,7,-diethylengycol in toluene. After purification of the product by vacuum destillaton the product is dissolved in toluene again and 1 mol allylalcohol is added and stirred at room temperature for 2 hours. The product is destined again and then hydrosilated to the trimetoxysilane as known by a person skilled in the art.

Surface-activated microscopic slides are silanised by incubation for 2 hours in a 1 g/l solution of the silane in toluene for 2 hours. Subsequently, the slides are washed three times in toluene and then heat treated for 2 hours at 130° C. Such slides are printed with amino-modified oligonucleotides and fixated in a moistured chamber at 50° C. for 2 hours. The GEETS slides are compared to slides treated with epoxypropyltrimetoxysilane. The increased wettability of the GEETS treated slides is significantly higher leading to an increased coupling of oligonucleotides on the surface and to a greater dot diameter Hybridization of such spots with complementary oligonucleotides results in a higher hybridisation signal on the GEETS treated slides.

What is claimed is:

1. A surface carrying a linker system comprising a compound for activating surfaces for bioconjugation having the following general formula (I):

wherein:

X is a reactive group capable of covalently binding to a surface and is selected from the group consisting of a $SiW_3$ group with W being a hydrolyzable atom or group, a group capable of forming free radicals on exposure to light, an anthrathione group or a derivative thereof, an anthraquinone group or a derivative thereof, and a benzophenone group or a derivative thereof;

Z is a reactive group capable of covalently binding to a biomolecule, is capable of nucleophilic substitution reactions, nucleophilic addition reactions, Diels-Alder reactions or radical substitutions, and is selected from the group consisting of a diene group, a dienophilic group, an aldehyde group, a hydroxyl group, a carboxylic acid group, an active ester group, an amino group, a thiol group, an aziridine group, an isocyanate group, an isothiocyanate group, an azide group, and a reactive leaving group;

X is not Z;

$Y_1$ and $Y_2$ are, independently from each other, $CR_1R_2$;

$R_1$ and $R_2$ are, independently from each other, H, $C_1$–$C_4$ alkyl, $C_1$–$C_4$ alkoxy or $C_1$–$C_4$ acyloxy;

i, j, and k are, independently from each other, an integer in the range from 1 to 10;

the total number of C atoms in $Y_1$ and $Y_2$, the C atoms of $R_1$ and $R_2$ not included, is in the range of 2 to 100;

Q is a hydrophilic atom or group selected from the group consisting of O, NH, C=O, O—C=O and $CR_3R_4$;

$R_3$ and $R_4$ are, independently from each other, selected from the group consisting of H, OH, $C_1$–$C_4$ alkoxy and $C_1$–$C_4$ acyloxy; and $R_3$ and $R_4$ are not H at the same time;

wherein when Q=NH, Z is not $NH_2$;

wherein when k>1, the Q's for each $[(Y_1)_i—Q—(Y_2)_j]_k$ are independently selected from each other; and wherein the linker system is covalently bonded to a biomolecule wherein said biomolecule is a partner of a specifically interacting system of complementary binding partners;

wherein said specifically interacting system of complementary binding partners is based on nucleic acid/complementary nucleic acid, peptide nucleic acid/nucleic acid, enzyme/substrate, receptor/effector, lectin/sugar, antibody/antigen, avidin/biotin or streptavidin/biotin interaction; and wherein said antibody is a polyclonal, monoclonal, chimeric or single-chain antibody or a functional fragment or derivative of such antibodies.

2. Surface according to claim 1, wherein said surface is selected from the group consisting of a $SiO_2$ surface of a silicon wafer, glass, quartz, fused silica, gold and a polymer.

3. Medical or diagnostic instrument comprising a surface according to claim 1.

4. Process for the detection of a biomolecule which is a partner of a specifically interacting system of complementary binding partners, comprising the steps of:

a) contacting a surface with a sample suspected to contain the complementary binding partner, b) removing non-specifically bound sample components in a washing step, and c) detecting specifically bound sample components;

wherein the surface carries a linker s stem comprising a compound for activating surfaces for bioconjugation having the following general formula (I):

(I)

wherein:

X is a reactive group capable of covalently binding to a surface and is selected from the group consisting of a $SiW_3$ group with W being a hydrolyzable atom or group, a group capable of forming free radicals on exposure to light, an anthrathione group or a derivative thereof, an anthraquinone group or a derivative thereof, and a benzophenone group or a derivative thereof;

Z is a reactive group capable of covalently binding to the biomolecule, is capable of nucleophilic substitution reactions, nucleophilic addition reactions, Diels-Alder reactions or radical substitutions, and is selected from the group consisting of a diene group, a dienophilic group, an aldehyde group, a hydroxyl group, a carboxylic acid group, an active ester group, an amino group, a thiol group, an aziridine group, an isocyanate group, an isothiocyanate group, an azide group, and a reactive leaving group;

X is not Z;

$Y_1$ and $Y_2$ are, independently from each other, H, $C_1R_2$;

$R_1$ and $R_2$ are, independently from each other, H, $C_1$–$C_4$ alkyl, $C_1$–$C_4$ alkoxy or $C_1$–$C_4$ acyloxy;

i, j, and k are, independently from each other, an integer in the range from 1 to 10;

the total number of C atoms in $Y_1$ and $Y_2$ the C atoms of $R_1$ and $R_2$ not included, is in the range of 2 to 100;

Q is a hydrophilic atom or group selected from the group consisting of O, NH, C=O—C=O and $CR_3R_4$;

$R_3$ and $R_4$ are, independently from each other, selected from the group consisting of H, OH, $C_1$–$C_4$ alkoxy and $C_1$–$C_4$ acyloxy; and $R_3$ and $R_4$ are not H at the same time;

wherein when Q=NH, Z is not $NH_2$;

wherein when k>1, the Q's for each $[(Y_1)_i—Q—(Y_2)_j]_k$ are independently selected from each other; and wherein the linker system is covalently bonded to the biomolecule and said biomolecule is a partner of a specifically interacting system of complementary binding partners.

5. Process according to claim 4 wherein for said detecting, a colored, fluorescent, bioluminescent, chemoluminescent, phosphorescent or radioactive label; an enzyme; an antibody or a functional fragment or derivative thereof, a protein A/gold based system; a biotin/avidin/streptavidin based system; or an enzyme electrode based system is used.

6. The method of claim 4, wherein said surface comprises a silicon oxide or gold.

7. Process for the isolation of a biomolecule which is a partner of a specifically interacting system of complementary binding partners, comprising the steps of:

a) contacting a surface with a sample suspected to contain the biomolecule complementary binding partner, b) removing non-specifically bound sample components in a washing step, and, optionally, c) eluting specifically bound sample components;

wherein the surface carries a linker system comprising a compound for activating surfaces for bioconjugation having the following general formula (I):

(I)

wherein:

X is a reactive group capable of covalently binding to a surface and is selected from the group consisting of a $SiW_3$ group with W being a hydrolyzable atom or group, a group capable of forming free radicals on exposure to light, an anthrathione group or a derivative thereof, an anthraquinone group or a derivative thereof, and a benzophenone group or a derivative thereof;

Z is a reactive group capable of covalently binding to the biomolecule, is capable of nucleophilic substitution reactions, nucleophilic addition reactions, Diels-Alder reactions or radical substitutions, and is selected from the group consisting of a diene group, a dienophilic group, an aldehyde group, a hydroxyl group, a carboxylic acid group, an active ester group, an amino group, a thiol group, an aziridine group, an isocyanate group, an isothiocyanate group, an azide group, and a reactive leaving group;

X is not Z;

$Y_1$ and $Y_2$ are, independently from each other, $CR_1R_2$;

$R_1$ and $R_2$ are, independently from each other, H, $C_1$–$C_4$ alkyl, $C_1$–$C_4$ alkoxy or $C_1$–$C_4$ acyloxy;

i, j, and k are, independently from each other, an integer in the range from 1 to 10;

the total number of C atoms in $Y_1$ and $Y_2$, the C atoms of $R_1$ and $R_2$ not included, is in the range of 2 to 100;

Q is a hydrophilic atom or group selected from the group consisting of O, NH, C=O, O—C=O and $CR_3R_4$;

$R_3$ and $R_4$ are, independently from each other, selected from the group consisting of H, OH, $C_1$–$C_4$ alkoxy and $C_1$–$C_4$ acyloxy; and $R_3$ and $R_4$ are not H at the same time;

wherein when Q=NH, Z is not $NH_2$;

wherein when k>1, the Q's for each $[(Y_1)_i$—Q—$(Y_2)_j]_k$ are independently selected from each other; and wherein the linker system is covalently bonded to the biomolecule and the biomolecule is a partner of a specifically interacting system of complementary binding partners.

8. A method of affinity chromatography comprising the steps of:

providing a surface as an affinity matrix; and performing affinity chromatography with the affinity matrix;

wherein the surface carries a linker system comprising a compound for activating surfaces for bioconjugation having the following general formula (I):

  (I)

wherein:

X is a reactive group capable of covalently binding to a surface and is selected from the group consisting of a $SiW_3$ group with W being a hydrolyzable atom or group, a group capable of forming free radicals on exposure to light, an anthrathione group or a derivative thereof, an anthraquinone group or a derivative thereof, and a benzophenone group or a derivative thereof;

Z is a reactive group capable of covalently binding to a biomolecule is capable of nucleophilic substitution reactions, nucleophilic addition reactions, Diels-Alder reactions or radical substitutions, and is selected from the group consisting of a diene group, a dienophilic group, an aldehyde group, a hydroxyl group, a carboxylic acid group, an active ester group, an amino group, a thiol group, an aziridine group, an isocyanate group, an isothiocyanate group, an azide group, and a reactive leaving group;

X is not Z;

$Y_1$ and $Y_2$ are, independently from each other, $CR_1R_2$;

$R_1$ and $R_2$ are, independently from each other, H, $C_1$–$C_4$ alkyl, $C_1$–$C_4$ alkoxy or $C_1$–$C_4$ acyloxy;

i, j, and k are, independently from each other, an integer in the range from 1 to 10;

the total number of C atoms in $Y_1$ and $Y_2$, the C atoms of $R_1$ and $R_2$ not included, is in the range of 2 to 100;

Q is a hydrophilic atom or group selected from the group consisting of O, NH, C=O, O—C=O and $CR_3R_4$;

$R_3$ and $R_4$ are, independently from each other, selected from the group consisting of H, OH, $C_1$–$C_4$ alkoxy and $C_1$–$C_4$ acyloxy; and $R_3$ and $R_4$ are not H at the same time;

wherein when Q=NH, Z is not $NH_2$;

wherein when k>1, the Q's for each $[(Y_1)_i$—Q—$(Y_2)_j]_k$ are independently selected from each other; and wherein the linker system is covalently bonded to a biomolecule and the biomolecule is a partner of a specifically interacting system of complementary binding partners.

9. A method of detecting a biomolecule comprising the steps of:

providing a sensor chip or biochip comprising a surface; and detecting a biomolecule with the sensor chip or biochip;

wherein the surface carries a linker system comprising a compound for activating surfaces for bioconjugation having the following general formula (I):

  (I)

wherein:

X is a reactive group capable of covalently biding to a surface and is selected from the group consisting of a $SiW_3$ group with W being a hydrolyzable atom or group, a group capable of forming free radicals on exposure to light, an anthrathione group or a derivative thereof, an anthraquinone group or a derivative thereof, and a benzophenone group or a derivative thereof;

Z is a reactive group capable of covalently binding to a biomolecule, is capable of nucleophilic substitution reactions, nucleophilic addition reactions, Diels-Alder reactions or radical substitutions, and is selected from the group consisting of a diene group, a dienophilic group, an aldehyde group, a hydroxyl group, a carboxylic acid group, an active ester group, an amino group, a thiol group, an aziridine group, an isocyanate group, an isothiocyanate group, an azide group, and a reactive leaving group;

X is not Z;

$Y_1$ and $Y_2$ are, independently from each other, $CR_1R_2$;

$R_1$ and $R_2$ are, independently from each other, H, $C_1$–$C_4$ alkyl, $C_1$–$C_4$ alkoxy or $C_1$–$C_4$ acyloxy;

i, j, and k are, independently from each other, an integer in the range from 1 to 10;

the total number of C atoms in $Y_1$ and $Y_2$, the C atoms of $R_1$ and $R_2$ not included, is in the range of 2 to 100;

Q is a hydrophilic atom or group selected from the group consisting of O, NH, C=O, O—C=O and $CR_3R_4$;

$R_3$ and $R_4$ are, independently from each other, selected from the group consisting of H, OH, $C_1$–$C_4$ alkoxy and $C_1$–$C_4$ acyloxy; and $R_3$ and $R_4$ are not H at the same time;

wherein when Q=NH, Z is not $NH_2$;

wherein when k>1, the Q's for each $[(Y_1)_i$—Q—$(Y_2)_j]_k$ are independently selected from each other; and wherein the linker system is covalently bonded to a biomolecule and the biomolecule is a partner of a specifically interacting system of complementary binding partners.

* * * * *